(12) United States Patent
Lee et al.

(10) Patent No.: US 10,386,080 B2
(45) Date of Patent: Aug. 20, 2019

(54) AIR CONDITIONER HAVING AN ION GENERATION DEVICE

(71) Applicant: LG ELECTRONICS INC., Seoul (KR)

(72) Inventors: Yanghwa Lee, Seoul (KR); Jieun Choi, Seoul (KR); Woojin Kim, Seoul (KR); Hyungho Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 793 days.

(21) Appl. No.: 14/410,401

(22) PCT Filed: Jun. 21, 2013

(86) PCT No.: PCT/KR2013/005486
§ 371 (c)(1),
(2) Date: Dec. 22, 2014

(87) PCT Pub. No.: WO2013/191499
PCT Pub. Date: Dec. 27, 2013

(65) Prior Publication Data
US 2015/0285515 A1 Oct. 8, 2015

(30) Foreign Application Priority Data
Jun. 21, 2012 (KR) .................. 10-2012-0066586

(51) Int. Cl.
*F24F 3/16* (2006.01)
*F24F 1/02* (2019.01)
(Continued)

(52) U.S. Cl.
CPC .............. *F24F 1/02* (2013.01); *F24F 1/0011* (2013.01); *F24F 3/166* (2013.01); *F24F 7/08* (2013.01);
(Continued)

(58) Field of Classification Search
USPC .................................................. 454/249, 156
See application file for complete search history.

(56) References Cited

U.S. PATENT DOCUMENTS 4,922,099 A * 5/1990 Masuda .................... B03C 7/04
250/324
5,055,118 A * 10/1991 Nagoshi .................... B03C 3/08
96/77
(Continued)

FOREIGN PATENT DOCUMENTS

CN 1371461 A 9/2002
CN 1728481 A 2/2006
(Continued)

*Primary Examiner* — Steven B McAllister
*Assistant Examiner* — Frances F. Hamilton
(74) *Attorney, Agent, or Firm* — Dentons US LLP (57) ABSTRACT

Provided is an air conditioner having an ion generation device, the ion generation device including a main body including an electrode structure that includes a discharge electrode and a ground electrode, a coupling part disposed on at least one surface of the main body, the coupling part being coupled to the case, and an ion discharge part disposed on the main body to discharge the ions generated when a high voltage is applied to the electrode structure.

8 Claims, 5 Drawing Sheets (51) Int. Cl.
  *F24F 1/0011* (2019.01)
  *F24F 7/08* (2006.01)
  *A61L 9/22* (2006.01)

(52) U.S. Cl.
  CPC ......... *A61L 9/22* (2013.01); *F24F 2003/1635* (2013.01); *F24F 2003/1682* (2013.01); *Y02A 50/21* (2018.01)

(56) References Cited

U.S. PATENT DOCUMENTS

| | | | | |
|---|---|---|---|---|
| 5,290,343 | A * | 3/1994 | Morita | B03C 3/86 96/39 |
| 5,385,761 | A * | 1/1995 | Iwanaga | C01B 13/11 427/448 |
| 7,256,979 | B2 * | 8/2007 | Sekoguchi | A61L 9/22 361/231 |
| 7,294,176 | B2 * | 11/2007 | Kim | B01D 53/32 96/69 |
| 7,316,735 | B2 * | 1/2008 | Tomimatsu | B03C 3/41 55/DIG. 38 |
| 7,453,682 | B2 * | 11/2008 | Kim | B03C 3/41 361/230 |
| 7,485,265 | B2 * | 2/2009 | Park | A01N 59/00 361/231 |
| 7,503,512 | B2 * | 3/2009 | Nakada | A61L 9/145 239/690 |
| 7,507,275 | B2 * | 3/2009 | Kim | B03C 3/017 361/230 |
| 7,916,445 | B2 * | 3/2011 | Sekoguchi | H01T 23/00 361/230 |
| 8,053,741 | B2 * | 11/2011 | Sekoguchi | H01T 23/00 250/423 F |
| 8,809,802 | B2 * | 8/2014 | Sung | H01T 23/00 250/423 R |
| 9,297,542 | B2 * | 3/2016 | Uehara | F24F 1/0007 |
| 9,452,236 | B2 * | 9/2016 | Miyamoto | A61L 9/22 |
| 9,474,822 | B2 * | 10/2016 | Jung | H05H 1/2406 |
| 2003/0072675 | A1 * | 4/2003 | Takeda | A61L 9/22 422/22 |
| 2005/0079112 | A1 * | 4/2005 | Li | B01D 53/9431 422/186.03 |
| 2006/0024219 | A1 * | 2/2006 | Park | A01N 59/00 422/186.04 |
| 2006/0042545 | A1 * | 3/2006 | Shibata | H01J 37/32009 118/722 |
| 2006/0056130 | A1 * | 3/2006 | Kim | A61L 9/015 361/230 |
| 2009/0027825 | A1 * | 1/2009 | Seto | B03C 3/383 361/213 |
| 2009/0042502 | A1 * | 2/2009 | Kim | B60H 3/0071 454/139 |
| 2009/0207548 | A1 * | 8/2009 | Seto | H01T 23/00 361/231 |
| 2009/0311008 | A1 * | 12/2009 | Adachi | G03G 15/0291 399/168 |
| 2011/0000251 | A1 * | 1/2011 | Oka | F24F 1/0011 62/404 |
| 2012/0006996 | A1 * | 1/2012 | Nishino | H01T 23/00 250/395 |
| 2012/0028561 | A1 * | 2/2012 | Takado | B03C 3/383 454/254 |
| 2012/0122389 | A1 * | 5/2012 | Kishimoto | F24F 1/0007 454/284 |
| 2012/0135674 | A1 * | 5/2012 | Uehara | F24F 1/0007 454/338 |
| 2012/0305799 | A1 * | 12/2012 | Sung | H01T 23/00 250/423 R |
| 2013/0147340 | A1 * | 6/2013 | Holbeche | A61B 18/042 313/231.31 |
| 2014/0204499 | A1 * | 7/2014 | Umeda | H05K 9/0067 361/220 |
| 2016/0015843 | A1 * | 1/2016 | Jang | B03C 3/12 62/264 |

FOREIGN PATENT DOCUMENTS

| | | | | |
|---|---|---|---|---|
| EP | 1 189 319 | A1 | 3/2002 | |
| EP | 1348448 | A1 | 10/2003 | |
| EP | 1852659 | A1 | 11/2007 | |
| EP | 2461112 | A1 | 6/2012 | |
| EP | 2033664 | B1 * | 11/2014 | ............... A61L 9/22 |
| JP | 7-313901 | A | 12/1995 | |
| JP | 08-0255668 | A | 10/1996 | |
| KR | 10-2002-0083566 | A | 11/2002 | |
| KR | 10-0452028 | B1 | 10/2004 | |
| KR | 10-2007-0044740 | A | 4/2007 | |
| KR | 10-2008-0072320 | A | 11/2008 | |
| KR | 20130068103 | A * | 6/2013 | |
| WO | 0116533 | A1 | 3/2001 | |

* cited by examiner

[FIG. 1]

PRIOR ART

AIR CONDITIONER HAVING AN ION GENERATION DEVICE

This application is a 35 USC § 371 National Stage entry of International Application No. PCT/KR2013/005486 filed on Jun. 21, 2013, and claims priority of Korean Application No. 10-2012-0066586, filed Jun. 21, 2012, both of which are hereby incorporated by reference in their entireties as if fully set forth herein.

TECHNICAL FIELD

The present disclosure relates to an air conditioner and a control method thereof.

BACKGROUND ART

Air conditioners are home appliances that maintain indoor air into the most proper state according to use and purpose thereof. For example, such an air conditioner controls indoor air into a cold state in summer and controls indoor air into a warm state in winter. Furthermore, the air conditioner controls humidity of the indoor air and purifies the indoor air to become into a pleasant and clean state. Air conditioners may have a refrigeration cycle constituted by a compressor, a condenser, an expansion device, and an evaporator.

As air conditioners are gradually expanded and used, consumers require products having high use efficiency, improved performances, and easy usability. Such an air conditioner may be classified into a split type air conditioner in which indoor and outdoor units are separated from each other and an integral type air conditioner in which indoor and outdoor units are integrally coupled to each other as a single device, according to whether the indoor and outdoor units are separated from each other.

Air conditioners are classified into a wall-mounted type air conditioner mounted on a wall, a frame type air conditioner, and a slim type air conditioner standing in the living room according to an installation method.

Also, air conditioners may be classified into a single-type air conditioner having capacity to operate one indoor unit so as to be used in a narrow place such as a home, a medium-large size air conditioner having very large capacity so as to be used in companies, cooking stores, or the like, and a multi-type air conditioner having capacity to sufficiently operate a plurality of indoor units.

A refrigeration cycle is performed in an air conditioner. The refrigeration cycle is constituted by a compressor compressing a refrigerant to a high pressure, a condenser condensing the refrigerant compressed in the compressor, an expansion device decompressing the refrigerant passing through the condenser to a low pressure, and an evaporator evaporating the refrigerant expanded in the expansion device.

Figure 1:
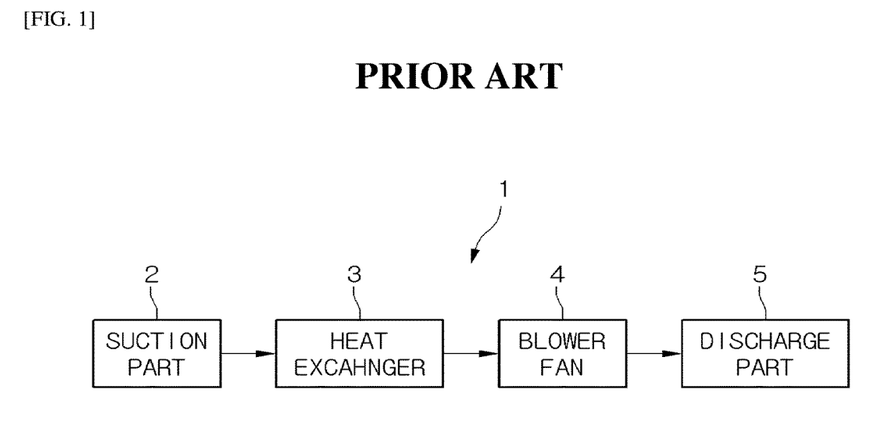
FIG. 1 is a block diagram of an air conditioner according to a related art.

Referring to FIG. 1, an indoor unit 1 of an air conditioner according to a related art includes a suction part 2 suctioning air, a heat exchanger 3 in which the suctioned through the suction part 2 is heat-exchanged, a discharge part 5 discharging the air heat-exchanged in the heat exchanger 3 into an indoor space, and a blower fan 4 generating an air flow form the suction part 2 to the discharge part 5. The blower fan 4 may be disposed at one position between the heat exchanger 3 and the discharge part 5.

The air discharged through the discharge part 5 may decrease in moisture while being heat-exchanged. Thus, there is a limitation that dried air is discharged to evaporate moisture existing in a skin of a user.

As a result, when the air conditioner is used for a predetermined time, the user's skin may be dried to allow the user to feel displeasure and speed up the aging of the skin.

DISCLOSURE OF INVENTION

Technical Problem

Embodiments provide an air conditioner having an improved structure to provide comfortability to a user and a control method thereof.

Solution to Problem

In one embodiment, an air conditioner includes: a case including a suction part; a discharging part disposed in the case to discharge air suctioned through the suction part; a discharge vane disposed at a side of the discharge part, the discharge vane being motionably provided to open or close the discharge part; and an ion generation device disposed inside the discharge vane to generate ions, wherein the ion generation device includes: a main body including an electrode structure that includes a discharge electrode and a ground electrode; a coupling part disposed on at least one surface of the main body, the coupling part being coupled to the case; and an ion discharge part disposed on the main body to discharge the ions generated when a high voltage is applied to the electrode structure.

In another embodiment, a method of controlling an air conditioner including an air suction part and a discharge part includes: turning the air conditioner on and inputting a mode set part to operate a specific mode under a preset operation condition; deciding a manual mode or an automatic mode with respect to the operation of the specific mode; operating an ion generation device provided in the discharge part; and when the specific mode is operated as the automatic mode, ending the operation of the specific mode after a set time elapses.

Advantageous Effects of Invention

According to the embodiments, the ion generation device may be disposed within the case of the indoor unit to generate the positive and negative ions. The generated positive and negative ions may be combined with water molecules within air to form water ions, thereby realizing the moisturizing effects with respect to the skin of the user.

Also, since the ion generation device is disposed on a side of the discharge part, the negative and positive ions together with the air to be discharged may be easily discharged into the indoor space.

Also, the ion generation device may include the electrode structure for generating ions to prevent the electrode from being oxidized and minimize a generation amount of ozone and power consumption.

Also, a specific mode for the skin care may be operated in the air conditioner. That is, the manual or automatic mode may be set to improve convenience of the user.

Also, while the skin care operation of the air conditioner is performed, when the preset operation conditions for maintaining the moisturizing effect are changed, whether the skin care operation is ended may be determined. Thus, the skin care operation may be continuously performed in a state where the skin care operation reaches the optimum effects.

MODE FOR THE INVENTION

Reference will now be made in detail to the embodiments of the present disclosure, examples of which are illustrated in the accompanying drawings. The invention may, however, be embodied in many different forms and should not be construed as being limited to the embodiments set forth herein; rather, that alternate embodiments included in other retrogressive inventions or falling within the spirit and scope of the present disclosure will fully convey the concept of the invention to those skilled in the art.

Figure 2:
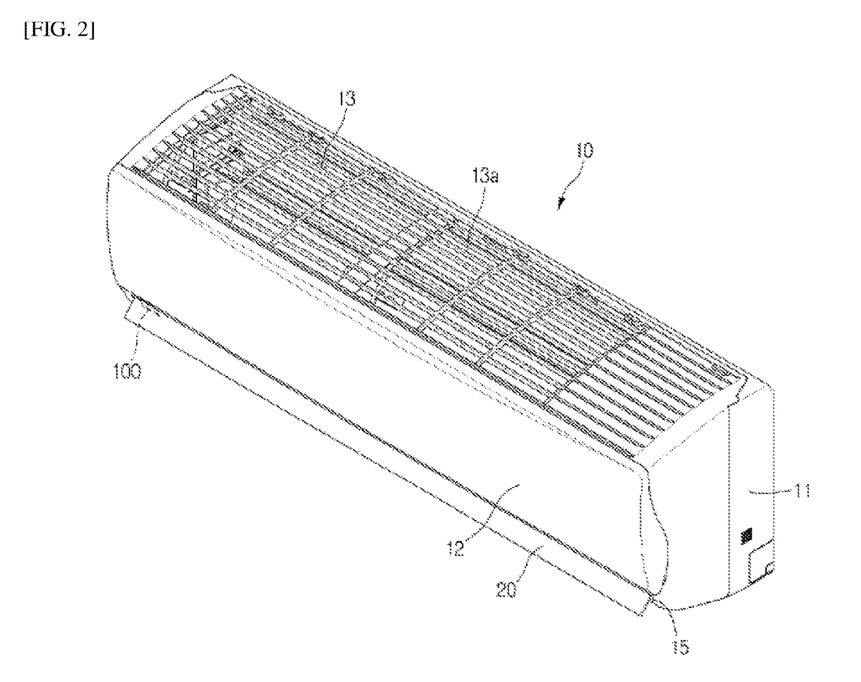
FIG. 2 is a perspective view of an air conditioner according to an embodiment.
Figure 3:
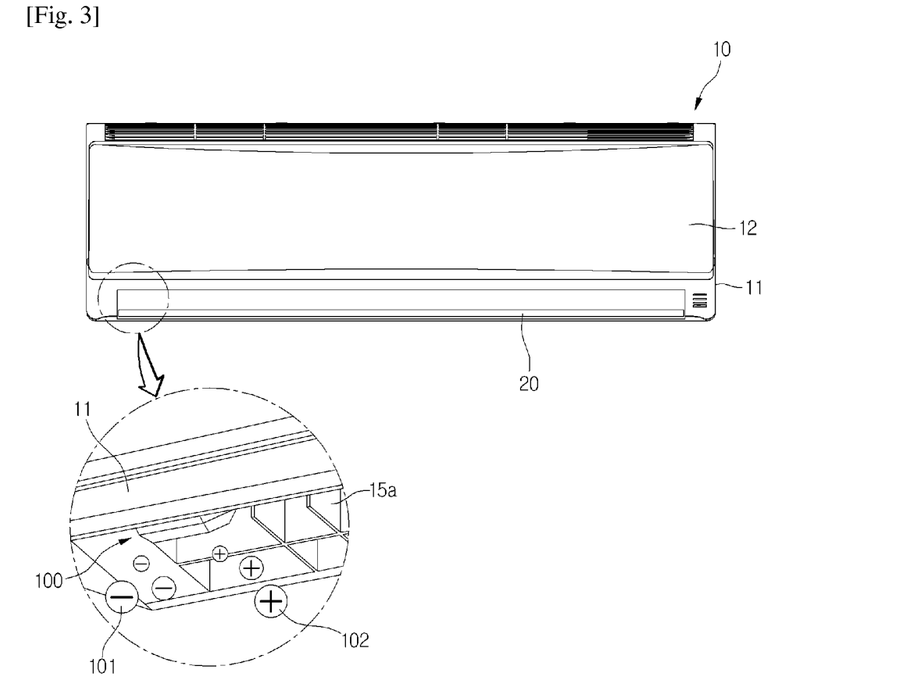
FIG. 3 is a view illustrating an arrangement of an ion generation device in the air conditioner according to an embodiment.

FIG. 2 is a perspective view of an air conditioner according to an embodiment, and FIG. 3 is a view illustrating an arrangement of an ion generation device in the air conditioner according to an embodiment.

Referring to FIGS. 2 and 3, an air conditioner 10 according to an embodiment includes a case 11 provided with a heat exchanger (not shown) and a blower fan (not shown) therein and a front panel 12 coupled to a front portion of the case 11 to defining a front outer appearance of the air conditioner 10. In a case of a split type air conditioner, the case 11 may be an indoor unit case disposed in an indoor space. On the other hand, in a case of an integral type air conditioner, the case 11 may be a case of the air conditioner itself.

The case 11 includes a suction part 13 through which indoor air is introduced and a discharge part 15 through which the air introduced through the suction part 13 is discharged into the indoor space after being heat-exchanged. At least one portion of an upper portion of the case 11 may be opened to define the suction part 13. Also, at least one portion of a lower portion of the case 11 may be opened to define the discharge part 15. Also, a suction grill 13a is disposed in the suction part 13, and a discharge grill 15a is disposed in the discharge part 15.

A discharge vane 20 that is movable to open or close the discharge part 15 is disposed on the outside the discharge part 15. When the discharge vane 20 is opened, air conditioned within the case 11 may be discharged into the indoor space. For example, a lower portion of the discharge vane 20 may be rotated upward to open the discharge vane 20.

An ion generation device 100 that generates ions to react with moisture of air is disposed on a side of the discharge part 15. The ion generation device 100 may be disposed outside or inside the discharge part 15 so that air discharged from the discharge part 15 passes through a peripheral portion of the ion generation device 100.

In other words, the ion generation device 100 may be disposed in a space between the discharge part 15 and the discharge vane 20, i.e., inside the discharge vane 20. That is, the ion generation device 100 may be disposed between the blower fan disposed within the case 11 and the discharge part 15.

Although the ion generation device 100 is disposed on a side end of the discharge part 15 in FIGS. 2 and 3, the present disclosure is not limited thereto. For example, the ion generation device 100 may be disposed at a central side of the discharge part 15. Alternatively, a plurality of ion generation devices may be disposed on the side end and central side of the discharge part 15.

When the discharge vane 20 is closed, the ion generation device 100 may be closed with respect to the outside. On the other hand, when the discharge vane 20 is opened, the ion generation device 100 may be opened with respect to the outside.

However, even though the discharge vane 20 is opened, since the ion generation device 100 is covered by the discharge vane 20 or at least one portion of the case 11, the ion generation device 100 may not be exposed to the outside. Thus, the air conditioner 10 may have an elegant outer appearance thereof.

When the ion generation device 100 operates, plasma discharge occurs in an electrode structure to generate negative ions 101 and positive ions 102. The negative ions 101 and the positive ions 102 together with the air discharged from the discharge part 15 may be provided into the indoor space. Hereinafter, the ion generation device will be described with reference to the accompanying drawings.

Figure 4:
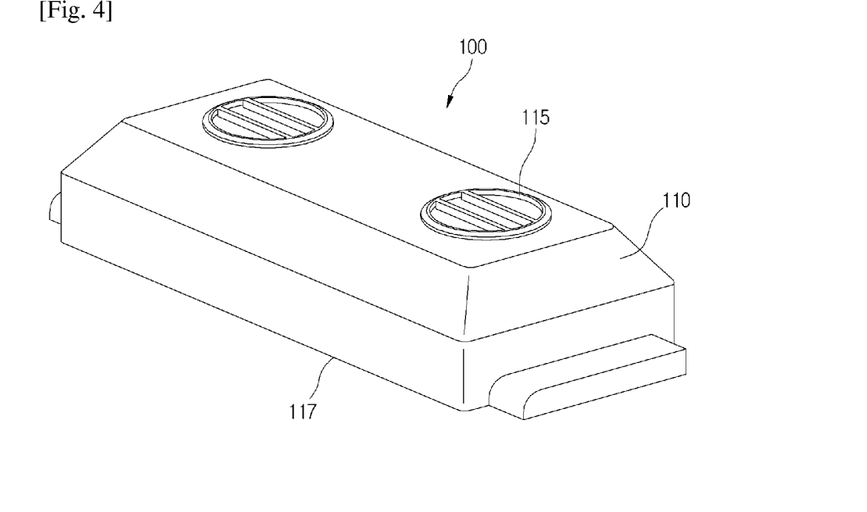
FIG. 4 is a view of the ion generation device according to an embodiment.
Figure 5:
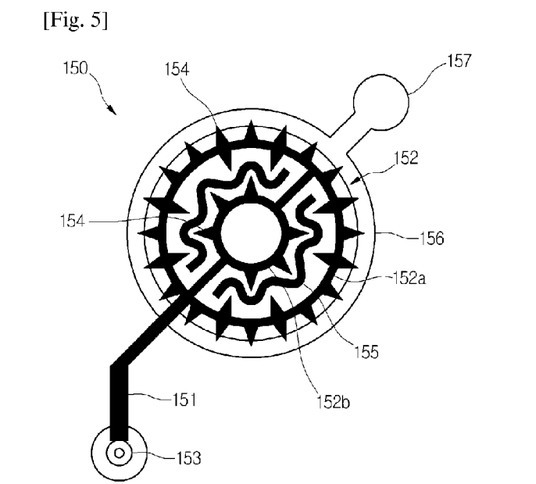
FIG. 5 is a view illustrating an electrode structure of the ion generation device according to an embodiment.

FIG. 4 is a view of the ion generation device according to an embodiment, and FIG. 5 is a view illustrating an electrode structure of the ion generation device according to an embodiment.

Referring to FIG. 4, the ion generation device 100 according to an embodiment includes a main body 110 defining an outer appearance thereof, a coupling part 117 disposed on one surface of the main body 110 and coupled to the air conditioner 10, and an ion discharge part 115 discharging ions generated within the main body 110. The coupling part 117 may adhere to the case 10 or the discharge part 15. Alternatively, the coupling part 117 may be coupled to the case 10 or the discharge part 15 by a separate coupling member.

An electrode structure 150 is disposed within the main body 110.

The electrode structure 150 includes a ceramic substrate (not shown) and two electrodes that are printed on both surfaces of the ceramic substrate. Also, the two electrodes include a discharge electrode 151 printed on one surface of the ceramic substrate and a ground electrode 156 printed on the other surface of the ceramic substrate.

The discharge electrode includes a pattern frame, an electrode part, and at least one discharge tip, and the ground electrode includes a pattern frame and an electrode part.

The pattern frame 152 of the discharge electrode 151 includes a closed external diagram 152a and a closed internal diagram 152b connected to and disposed within the external diagram 152a. Also, each of the external and internal diagrams 152a and 152b includes at least one discharge tip 154.

The external or internal diagram 152a and 152b may represent a circular shape, an oval shape, or a polygonal shape. Also, the external diagram and the internal diagram may be disposed so that they do not overlap each other. For example, the external diagram and the internal diagram may have the same shape.

Each of the external and internal diagrams includes the at least one discharge tip 154. Here, a ratio (K1/K2) of the number K1 of discharge tips disposed on the external diagram to the number K2 of discharge tips disposed on the internal diagram may be about 4:5. In this case, an ion generation amount under the same applied voltage may increase.

The discharge electrode 151 may be printed by using metal oxide paste. A metal material within the metal oxide paste may be selected from the group consisting of tungsten, iron, copper, platinum, and silver. For example, the metal material may be silver (Ag).

The discharge electrode may be printed by using silver oxide paste. Since the silver oxide paste has low resistance of about 10Ω to about 20Ω, the discharge may be easily performed. Thus, the discharge may be uniformly performed over the while electrode. In addition, the silver oxide paste may reduce an amount of ozone by the discharge.

An ion generation amount of the ion generation device including the electrode structure may be greater than that of an ion generation device according to a related art. Particularly, the ion generation amount of the ion generation device according to the current embodiment may be greater by about 4 times to eight times than that of a tip electrode according to the related art. In addition, when the ion generation device including the electrode structure is used, power consumption may be minimized to a range of about 2 W to about 5 W due the above-described characteristics. Also, as the silver oxide paste is used, since the silver oxide paste restrains the generation of the ozone that is mainly generated around the discharge electrode, the ozone generation amount may be significantly reduced when compared to that of the ion generation device according to the related art.

The discharge electrode 151 may include a discharge electrode part 153 and a discharge obstacle 155. The discharge obstacle 155 may be printed by using the same metal oxide paste as that of the discharge electrode 151. Also, the discharge obstacle 155 and the discharge electrode 151 may be printed at the same time. The discharge obstacle 155 may be disposed between the external diagram 152a and the internal diagram 152b to interrupt discharge interference between the discharge tip of the external diagram and the discharge tip of the internal diagram when discharged.

The ground electrode 156 includes a pattern part and a ground electrode part 157. The ground electrode 156 may be printed through the same printing method as that of the discharge electrode 151. Also, the ground electrode 156 may be screen-printed by using the metal oxide paste.

Referring to FIG. 5, the ground electrode part 157 of the ground electrode 156 and the discharge electrode part 153 of the discharge electrode 151 may face each other and be respectively disposed on both extreme ends of the electrode structure 150. When the ground electrode part 157 and the discharge electrode part 153 are respectively disposed on both extreme ends of the electrode structure 150, a distance between both electrodes may be maximally secured. Thus, abnormal discharge that may occur between the discharge electrode 151 and the ground electrode 156 may be prevented, and also, power consumption may be reduced.

An effect of the ion generation device 100 will be described simply.

When a high voltage is applied into the electrode structure 150, high electrical fields may be formed around the electrode structure 150. Thus, free electrons passing around the electrode structure 150 may be accelerated to collide with neutral molecules (oxygen, nitrogen, and the like) within air, thereby ionizing the molecules.

The ionized molecules may act as condensed cores and be combined with moisture of air to form water ion clusters. Since a skin of the human body has a potential difference less than that of the water ion cluster, the water ion clusters may be transferred into the skin.

Each of the water ion clusters has a mean particle size of about 10 nm to about 20 nm. On the other hand, since a distance between cytoplasm existing in the skin is about 70 nm, the water ion clusters may be permeated into corneum to form a nano mist coating membrane. The nano mist coating membrane may maintain moisture of the corneum, and thus allow the skin to be moisturized.

The ionized molecules collide with surfaces of bacteria or viruses to form OH radicals. Here, the formed OH radicals may be combined with hydrogen ions of the surfaces of the bacteria or viruses to form water molecules, thereby activating the bacteria or viruses.

Also, the OH radicals may remove bad smell substances such as cigarette smoke. The bad smell substances such as cigarette smoke may chemically react with the generated OH radicals and then be dissolved into $H_2O$ and $CO_2$ which are harmless to human body and thus removed.

The ion generation apparatus 100 may discharge positive ions and negative ions at the same time. The discharged ions may act as cores for forming the clusters and prevent secondary pollutants such as ozone and nitrogen oxide from occurring. Also, the discharged ions may continuously provide beneficial air in metabolism of the human body in addition to deodorization, sterilization, and the like.

In detail, an input voltage of about DC 12 V may be primarily boosted so that a ceramic transformer is oscillated through an autotransformer. Then, the input voltage may be secondarily boosted through the oscillated ceramic transformer to output a high voltage of about several kV. The outputted high voltage may be applied into the ceramic discharge electrode 151 to generate positive and negative ions.

Figure 6:
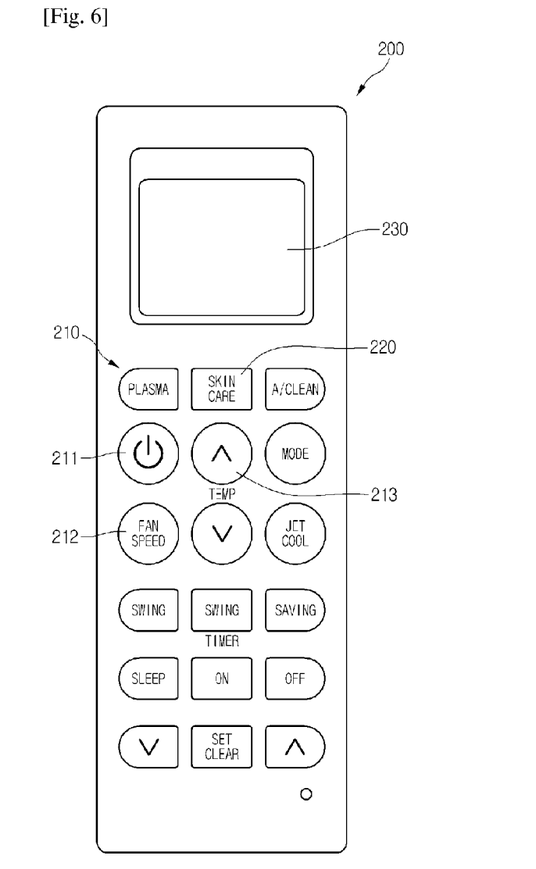
FIG. 6 is a view of a remote controller for controlling the air conditioner according to an embodiment.

FIG. 6 is a view of a remote controller for controlling the air conditioner according to an embodiment.

Referring to FIG. 6, the air conditioner 10 according to an embodiment may be controlled in operation by a remote controller 200.

The remote controller 200 includes a main body 201, an input unit 210 disposed on one surface of the main body 201 to input a predetermined command for operating the air conditioner 10, and a display unit 230 displaying an operation state of the air conditioner 10.

The input unit 210 includes a power input part 211 for turning power of the air conditioner 10 on/off, a wind amount set part 212 adjusting an amount of wind discharged from the discharge part 15, and a temperature set part 213 adjusting a set temperature of an indoor space.

The input unit 210 includes a mode set part 220 setting a specific operation mode of the air conditioner 10.

For example, the specific operation mode may be a "skin care mode" that provides moisturizing effects to a user because the ion generation device 100 generates negative and positive ions 101 and 102 to supply the generated ions into an indoor space.

The air conditioner 10 may further include a control unit controlling an operation of the air conditioner 10 by manipulating the remote controller 200. Hereinafter, a control method of the air conditioner 10 when the skin care mode is operated will be described with reference to the accompanying drawings.

Figure 7:
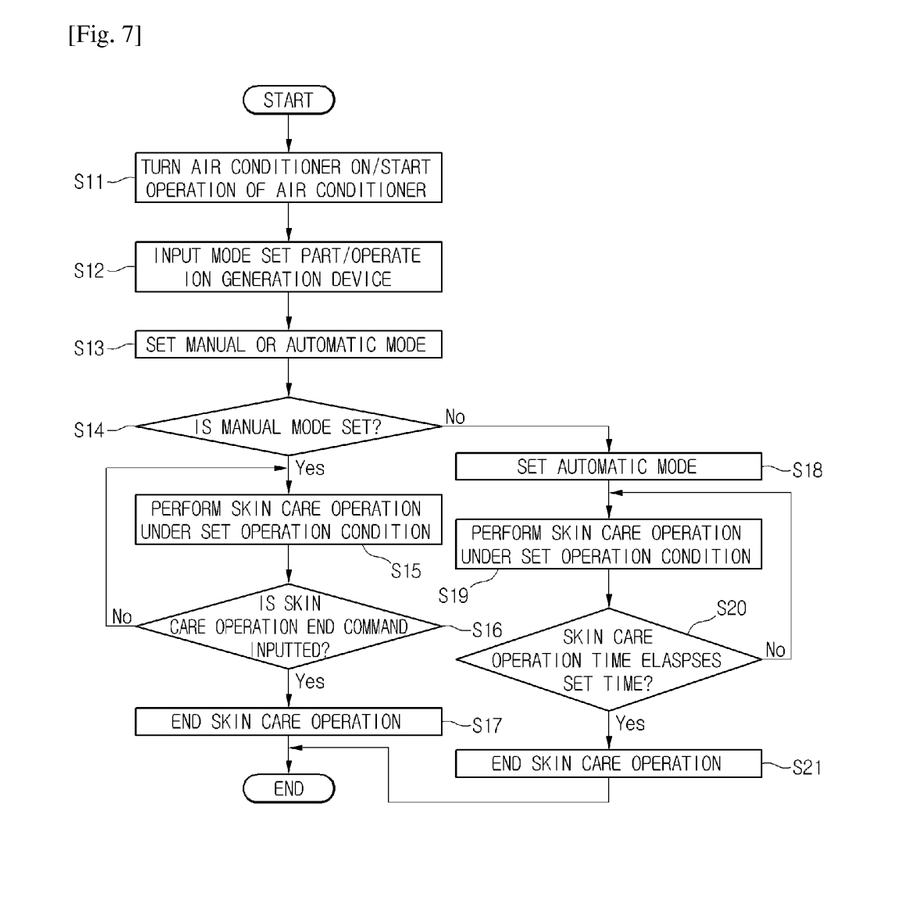
FIG. 7 is a flowchart illustrating a control method of an air conditioner according to a first embodiment.

FIG. 7 is a flowchart illustrating a control method of an air conditioner according to a first embodiment. Referring to FIG. 7, a control method according to a first embodiment will be described.

An air conditioner 10 is turned on and starts an operation thereof (S11).

Also, a mode set part 220 is inputted to operate a scan care mode. When the skin care mode is operated, an ion generation device 100 may be operated. That is, a high voltage is outputted and applied into a discharge electrode 151 to generate negative ions 101 and positive ions 102. The negative and positive ions 101 and 102 may be discharged to the outside of the device through an ion discharge part 115 (S12).

The skin care mode may be set to a manual mode or an automatic mode. The manual mode may be a mode in which an operation of the skin care mode is decided by a command of a user. The automatic mode may be a mode in which an operation of the skin care mode is decided by an operation time of the air conditioner.

In the selection of the manual mode or automatic mode, when the mode set part 220 is inputted once again after the mode set part 220 is inputted, the automatic mode may be set. For another example, when the mode set part 220 is inputted, a screen on which the manual mode or automatic mode is selected is displayed on the display unit 230. Here, the manual mode or automatic mode may be selected by using a direction key of the temperature set part 230.

Although the manual mode or automatic mode is set after the ion generation device 100 is operated (S12) in the drawings, the present disclosure is not limited thereto. For example, the ion generation device 100 may be operated after the manual or automatic mode is set.

When the manual mode is set (S14), the air conditioner 10 may perform the skin care operation under the preset operation conditions. In the preset operation conditions, an ON operation of the ion generation device 100, a temperature of an indoor space, moisture, a wind amount, and an opened angle of a discharge vane 20 may be set as set values. For example, an indoor temperature of about 25° C., moisture of about 60%, a large amount of wind, and an opened angle of about 10° for the discharge vane 20 may be set. These set values may be understood as conditions that are capable of maximizing skin moisturizing effects.

As a result, since the skin care mode is operated under the above-described conditions, ions discharged into the indoor space and water molecules may be combined with each other to generate water ion clusters. Then, the generated water ion clusters may act on a skin of the user to realize skin refreshing (S15).

Also, while the manual mode is operated, when a skin care operation end command is inputted by the user, the skin care operation may be ended (S16 and S17).

When the automatic mode is set in the operation S14 (S16), the skin care operation may be performed under the same operation condition as that in operation S15.

When the skin care operation is performed, the operation time may be integrated. When the integrated operation time elapses a set time, the skin care operation may be automatically ended. For example, the set time may be two hours or less.

When the skin care operation is continuous for the set time, it may be determined that the skin moisturizing effect reaches a predetermined level or more. When the ion generation device 100 is operated for a long time, power consumption may excessively increase. Thus, the skin care operation may be ended after the set time elapses to prevent the above-described limitation from occurring. Also, the automatic mode may be selectively performed as described in operation S13 (S20 and S21).

Figure 8:
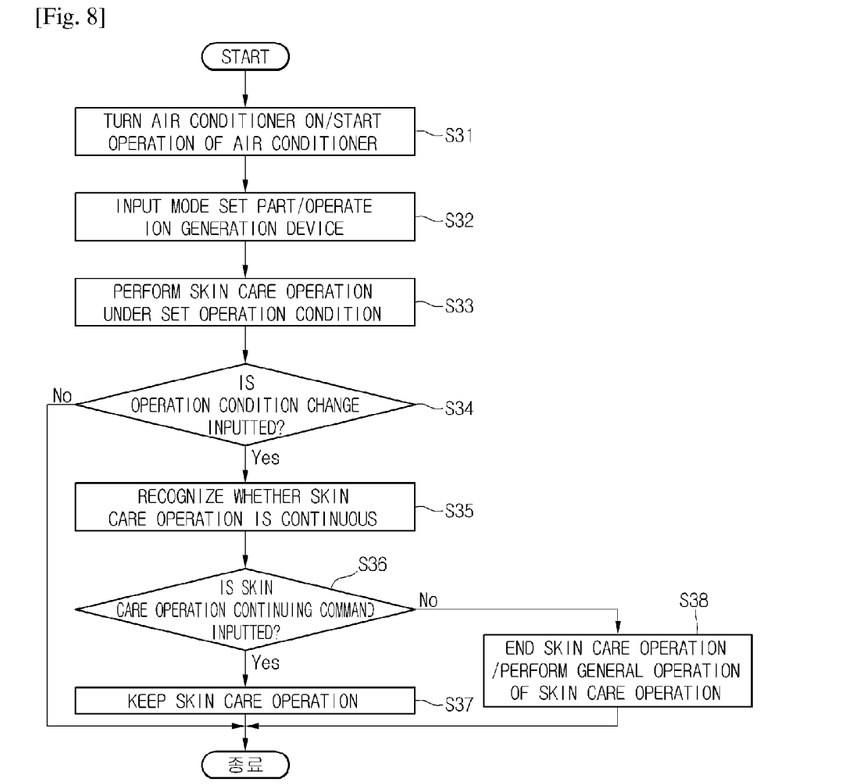
FIG. 8 is a flowchart illustrating a control method of an air conditioner according to a second embodiment.

FIG. 8 is a flowchart illustrating a control method of an air conditioner according to a second embodiment. Referring to FIG. 8, a control method according to a second embodiment will be described.

An air conditioner 10 is turned on and starts an operation thereof (S31). Also, a mode set part 220 is inputted to operate a scan care mode. When the skin care mode is operated, an ion generation device 100 is operated, and then, the air conditioner 10 performs the skin care operation under preset operation conditions. The descriptions with respect to the preset operation conditions will be denoted by those of the first embodiment (S32 and S33).

While the skin care mode is operated, a user may recognize whether the operation conditions of the air conditioner 10 are changed. For example, the user may recognize whether at least one value of a set temperature of an indoor space, a wind amount, and an opened angle of a vane is changed.

When the at least one value is changed, an effect of the skin care mode may be reduced. Thus, whether the air conditioner 10 continuously performs the skin care operation may be inputted. For example, information for asking whether the skin care operation is continuously performed or not may be displayed on a display unit 230. The user may select whether the skin care operation is continuous (S34 and S35).

When a command for performing the continuous skin care operation is inputted by the user, the skin care operation may be continuously performed (S36 and S37).

On the other hand, when the command for performing the continuous skin care operation is not imputed, the skin care operation is ended, and thus, a general operation of the air conditioner 10 may be performed. Here, the general operation of the air conditioner may be understood as a cooling or heating operation on the basis of the changed operation conditions (S38).

The control method according to the second embodiment may be performed by being combined with that of the first embodiment. That is, when the operation conditions are changed while the manual or automatic mode according to the first embodiment is performed, the control method as shown in FIG. 8 may be performed.

Figure 9:
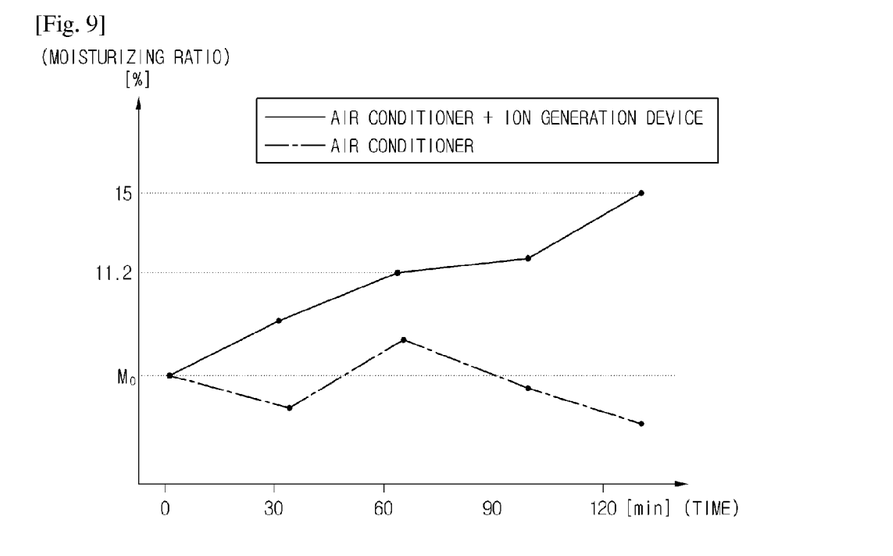
FIG. 9 is an experimental graph illustrating a moisturizing effect of an air conditioner including an ion generation device according to an embodiment.

FIG. 9 is an experimental graph illustrating a moisturizing effect of an air conditioner including an ion generation device according to an embodiment.

FIG. 9 is a graph illustrating a moisturizing effect that is capable of being obtained in a skin of a user when an air conditioner 10 includes an ion generation device 100. A horizontal axis (an X axis) represents a time elapsing after the air conditioner or the ion generation device 100 is operated, and a vertical axis (a Y axis) represents a value in which a moisturizing effect (a moisturizing ratio) of a skin of a user is indicated as a predetermined value according to a certain reference.

In the vertical axis, a moisturizing ratio Mo represents a mean moisturizing ratio. That is, the moisturizing ratio Mo may be a reference moisturizing ratio that is measured in the skin of the user at a time point at which an experiment starts. Also, a percent (%) value may be a value of an increased moisturizing ratio with respect to the moisturizing ratio Mo.

When an air conditioner 10 is operated alone, e.g., when an ion generation device 100 is not provided in the air conditioner 10 or is not operated, a moisturizing ratio may decrease as time passes, and then increase. Then, the moisturizing ratio may decrease again. Thus, when an operation time of the air conditioner 10 elapses two hours, a skin moisturizing ratio of the user may be reduced than the initial moisturizing ratio Mo.

On the other hand, when the air conditioner 10 and the ion generation device 100 are operated together, it is seen that a moisturizing ratio continuously increases from the initial moisturizing ratio Mo. Therefore, the ion generation device 100 may be provided in the air conditioner 10 to supply ions into the indoor space, thereby improving the skin moisturizing effect by the water ion clusters.

INDUSTRIAL APPLICABILITY

According to the embodiments, the ion generation device may be disposed within the case of the indoor unit to generate the positive and negative ions. The generated positive and negative ions may be combined with water molecules within air to form water ions. Thus, since the moisturizing effects with respect to the skin of the user may be realized, industrial applicability may be remarkable.

The invention claimed is:

1. An air conditioner comprising:
a case comprising a suction part;
a discharging part disposed in the case to discharge air suctioned through the suction part;
a discharge vane disposed at a side of the discharge part, the discharge vane being motionably provided to open or close the discharge part; and
an ion generation device disposed within the discharging part to generate ions, wherein the ion generation device comprises:
a main body comprising an electrode structure;
a coupling part disposed on at least one surface of the main body, the coupling part being coupled to the case; and
an ion discharge part disposed on the main body to discharge the ions generated when a high voltage is applied to the electrode structure, wherein the electrode structure comprises:
a ceramic substrate;
a discharge electrode disposed on a first surface of the ceramic substrate, the discharge electrode comprising a discharge electrode part and at least one discharge tip; and
a ground electrode disposed on a second surface of the ceramic substrate, the ground electrode comprising a ground electrode part,
wherein the discharge electrode comprises a pattern frame on which a plurality of diagrams are disposed,
the pattern frame comprises an external diagram and an internal diagram disposed within the external diagram and not in contact with the external diagram, and
each of the external and internal diagrams provided in a closed configuration and includes at least one a discharge tip.

2. The air conditioner according to claim 1, wherein the ion generation device is covered with respect to ambient in a state where the discharge vane is closed and wherein the ion generation device is opened with respect to the ambient in a state where the discharge vane is opened.

3. The air conditioner according to claim 1, wherein the ion generation device may be a plurality of ion generation devices provided within the discharging part.

4. The air conditioner according to claim 1, wherein the ions comprise negative and positive ions generated by ionizing neutral molecules within air, and the negative and positive ions are combined with moisture of the air to bind and to form water ion clusters.

5. The air conditioner according to claim 1, wherein the external diagram and the internal diagram may be disposed so that they do not overlap each other.

6. The air conditioner according to claim 1, wherein the external diagram and the internal diagram have the same shape.

7. The air conditioner according to claim 1, wherein the discharge electrode comprises a discharge obstacle disposed between the external diagram and the internal diagram to interrupt discharge interference between the discharge tip of the external diagram and the discharge tip of the internal diagram.

8. The air conditioner according to claim 1,
wherein a ratio of the number of discharge tips disposed on the external diagram to the number of discharge tips disposed on the internal diagram is 4 to 5.

* * * * *